United States Patent

Miura et al.

[11] Patent Number: 5,583,635
[45] Date of Patent: Dec. 10, 1996

[54] METHOD OF MEASURING PARTICLES AND APPARATUS FOR THE SAME

[75] Inventors: Yasuhiro Miura, Chiba; Yutaka Shiomi, Ichihara; Masao Morikawa; Akira Morisaki, both of Sodegaura, all of Japan

[73] Assignee: Sumitomo Chemical Company, Limited, Osaka, Japan

[21] Appl. No.: 238,000

[22] Filed: May 4, 1994

[30] Foreign Application Priority Data

May 11, 1993 [JP] Japan ................ 5-109372

[51] Int. Cl.$^6$ ................................ G01N 15/02
[52] U.S. Cl. ................ 356/338; 356/339; 377/11
[58] Field of Search ................ 356/335–343, 356/38; 377/10, 11

[56] References Cited

U.S. PATENT DOCUMENTS

| | | | |
|---|---|---|---|
| 3,579,249 | 5/1971 | Dewey | 356/335 |
| 4,021,117 | 5/1977 | Grohde et al. | 377/10 |
| 4,330,745 | 5/1982 | Hayashi | 377/10 |
| 5,059,395 | 10/1991 | Brittenham et al. | 356/335 |
| 5,257,087 | 10/1993 | Furuya | 356/336 |

*Primary Examiner*—Hoa Q. Pham
*Attorney, Agent, or Firm*—Birch, Stewart, Kolasch & Birch, LLP

[57] ABSTRACT

The present invention provides a method of measuring particles and an apparatus for the same, which count only particles in liquid by distinguishing between the particles and bubbles in liquid. In order to fulfill the above requirements, in the present invention, liquid to be measured flows through a flow cell at a fixed flow rate, and a laser beam is irradiated thereto. Scattering light is generated when particles and bubbles pass through a laser beam irradiation region, and the scattering light is converted into a pulse signal by a photoelectric converter. In the pulse signals, a pulse signal having a pulse width of 100 μS is regarded as corresponding to light scattered by a bubble, which is omitted from the number of pulse signals. Thus, only a pulse signal corresponding to light scattered by a particle in liquid can be measured.

13 Claims, 11 Drawing Sheets

SAMPLE LIQUID

METHOD OF MEASURING PARTICLES AND APPARATUS FOR THE SAME

BACKGROUND OF THE INVENTION

1. Field of the Invention

The present invention relates to a method of measuring particles and an apparatus for the same, which measure the particles in liquid by irradiating a laser beam to the liquid which flows at a fixed flow rate, and detecting light scattered by the particles in the liquid.

2. Related Background Art

In dynamic RAM (DRAM), integration density of integrated circuits (ICs) is shifted from 16M to 64M because of the progress of manufacturing techniques for semiconductor integrated circuits. As the ICs are highly integrated, IC design geometries have been shrinking. In the manufacture of IC, as one of means to improve the yield, it has been known that to improve the purity of chemicals for electronic industries which are used in cleaning wafers and in etching is effective. Evaluation of the purity requires techniques for measuring particles (foreign substances) present in chemicals, which requires the improvement of the accuracy of the particle measuring apparatus and the reliability. Conventionally, such a particle measuring method generally employs the following scattering light detecting method.

That is, the chemical for electronic industries, which is a sample, flows continuously in a flow cell at a fixed flow rate, and a laser beam irradiates to the liquid, which flows in the flow cell, in a direction perpendicular to a direction of the flow of the liquid. When the laser beam is irradiated to the particle present in the chemical, light scattering occurs by the particle. FIG. 1 is a sectional view typically showing a part of the measuring system, and while a particle 2 in sample liquid which passes through a flow cell 1 passes through the irradiation region, light scattering occurs. The light scattering converges in a light detector such as a photomultiplier through an optical system and is converted into a pulse signal. Therefore the particle concentration in chemical is measured by counting the number of pulse signals obtained in the light detector.

However, the particle concentration in the sample is not measured accurately by the conventional scattering light detecting method. That is, because not only are particles but also bubbles present in the sample liquid, the light scattering obtained by irradiating the laser beam include light scattering which is generated by the bubbles. Accordingly, even though the number of pulse signals obtained in accordance with the particles is counted, the pulse signals in accordance with the bubbles are also counted. Therefore, the measurement of the particle concentration may appear too high.

For example, when the chemical is hydrogen peroxide ($H_2O_2$), because the chemical is not stable, bubbles (oxygen) are easily generated and this results are not reliable. Since ammonia solution of 30 wt % (weight percentage) has a low boiling point, bubbles are easily generated and therefore accurate results cannot be obtained as well. When such an unstable sample liquid passes through the flow cell the center of which is narrow, its flow rate increases and the pressure is lowered. Therefore, more bubbles are generated. Thus, in the measurement of the particle concentration in a liquid, e.g., hydrogen peroxide, ammonia solution, in which the bubbles are easily generated, it is hard to accurately measure the particles until the bubbles are distinguished therefrom.

Conventionally, in order to solve these problems, a countermeasure of cooling sample liquids, and various other countermeasures have been considered.

First, there is one countermeasure shown in FIG. 2, in which a resin tube 4 having minute blow holes is used. That is, the resin tube 4 is placed in vacuum, and the sample liquid flows in the resin tube 4, whereby the bubbles in the sample liquid are drawn into vacuum through the minute blow holes. After the bubbles are removed, the particle concentration is measured.

Further, there is another countermeasure shown in FIG. 3. That is, the bubbles in the liquid are removed by injecting the sample liquid from a spray nozzle 5, and thereafter the number of particles is counted by a particle counter PCM.

It is preferable that a general control level of particles in the electronic industrial chemical is below 10~100 pieces/ml. However, in any cases of the above-described countermeasures, it is hard to remove bubbles to a level which does not have effects on the particle measurement.

SUMMARY OF THE INVENTION

Because it is hard to remove bubbles physically to a certain level in all possible means, in the present invention, particles are measured without deforming. That is, a laser beam is irradiates the sample liquid, and light scattering corresponding to particles in liquid and light scattering corresponding to bubbles are distinguished among light scattering obtained by irradiating a laser beam, and then the particles are measured.

In the present invention, a method of measuring the number (a numeral value) of particles in liquid, comprising the steps of: flowing the liquid including particles at a predetermined rate; irradiating a laser beam into the liquid; detecting light scattering from the liquid; converting the detected light scattering into pulse signals, obtaining the number of the pulse signals having a pulse width (time period) shorter than a predetermined value (time period).

Further, the obtaining step comprises the steps of: counting the number of both of narrow-width pulse signals and wide-width pulse signals as an all pulse value, the narrow-width pulse signals having a pulse width shorter than a predetermined value and the wide-width pulse signals having a pulse width longer than the predetermined value; and counting the number of the wide-width pulse signals as an wide-width pulse value.

Of course, the above-mentioned method further comprises a step of subtracting the wide-width pulse value from the all pulse value. So, the result of this subtracting step corresponds to the number of the particles.

In a preferred embodiment, the present relates to, a method of measuring the number of particles in liquid comprising: a first step of flowing the liquid containing particles at a fixed rate; a second step of irradiating a laser beam to the liquid; a third step of converting light scattering from the liquid generated by the irradiating laser beam into pulse signals; a fourth step of counting the number of the pulse signals; a fifth step of selecting the pulse signal having the pulse width larger than a predetermined value; and a sixth step of subtracting the number of the pulse signals selected in the fifth step from the number obtained in the fourth step, whereby a result of the subtraction is the number of particles in the liquid.

Another embodiment of the invention is a method of measuring the number of particles in liquid comprising: a first step of flowing the liquid containing particles at a fixed rate; a second step of irradiating a laser beam to the liquid; a third step of converting light scattering from the liquid generated by the irradiating laser beam into pulse signals; a fourth step of selecting the pulse signals having the pulse width shorter than a predetermined value; and a fifth step of counting the number of the pulse signals selected as shorter than a predetermined value, in the fourth step whereby a result of the counting is the number of particles in the liquid.

A further embodiment is a method of measuring the number of particles in liquid comprising: a first step of flowing the liquid containing particles at a fixed rate; a second step of irradiating a laser beam to the liquid; a third step of converting light scattering from the liquid generated by the irradiating laser beam into pulse signals; a fourth step of counting the number of the pulse signals; a fifth step of selecting the pulse signal having a waveform comprising a plurality of waves from the pulse signals; and a sixth step of subtracting the number of the pulse signals selected in the fifth step from the number obtained in the fourth step, whereby a result of the subtraction is the number of particles in the liquid.

Another embodiment is a method of measuring the number of particles in liquid comprising: a first step of flowing the liquid containing particles at a fixed rate; a second step of irradiating a laser beam to the liquid; a third step of converting light scattering from the liquid generated by the irradiating laser beam into pulse signals; a fourth step of selecting a pulse signal having the waveform comprising a single wave from the pulse signals; and a fifth step of counting the number of the pulse signals selected in the fourth step whereby a result of the counting is the number of particles in the liquid.

Another aspect of the present invention is an apparatus for measuring the number of particles in a liquid comprising: a passage for the liquid containing particles and flowing at a fixed flow rate; a light source for irradiating a laser beam to the liquid flowing through the passage; light detecting means for converting light scattering from the liquid obtained by irradiating the laser beam into pulse signals; pulse width detecting means for detecting a pulse width of a pulse signal output from the light detecting means; and selecting means for removing a pulse signal having a pulse width larger than a predetermined value from the pulse signals detected by the light detecting means.

A further embodiment is a apparatus for measuring the number of particles in a liquid comprising: a passage for a liquid containing particles and flowing at a fixed flow rate; a light source for irradiating a laser beam to the liquid flowing through the passage; light detecting means for converting light scattering from the liquid, obtained by irradiating the laser beam, into pulse signals; pulse width detecting means for detecting a pulse width of a pulse signal outputted from the light detecting means; and selecting means for selecting a pulse signal having a pulse width shorter than a predetermined value from the pulse signals detected by the light detecting means.

An additional embodiment is an apparatus for measuring the number of particles in a liquid comprising: a passage for a liquid containing particles and flowing at a fixed flow rate; a light source for irradiating a laser beam to the liquid flowing through the passage; light detecting means for converting light scattering from the liquid obtained by irradiating the laser beam into pulse signals; waveform detecting means for detecting the waveform of the pulse signal outputted from the light detecting means; and selecting means for removing the pulse signal having a waveform comprising a plurality of waves from the pulse signals.

Another embodiment is an apparatus for measuring the number of particles in a liquid comprising: a passage for a liquid containing particles and flowing at a fixed flow rate; a light source for irradiating a laser beam to the liquid flowing through the passage; light detecting means for converting light scattering from the liquid obtained by irradiating the laser beam into pulse signals; waveform detecting means for detecting the waveform of the pulse signal outputted from the light detecting means; and selecting means for removing the pulse signal a having waveform comprising a single wave from the pulse signals.

According to the present invention, a pulse signal obtained corresponding to light scattered by a particle in liquid has a stable short pulse width under the condition that a flow rate of liquid is maintained, and its waveform has a single wave. On the other hand, a pulse signal obtained corresponding to light scattered by a bubble in liquid has a pulse width larger than that of the pulse signal corresponding to the particle, and its waveform has a plurality of waves.

Thus, since a pulse width and pulse waveform of a pulse signal obtained corresponding to light scattering are different in the case of the particle and in the case of bubble, the particle and bubble can be distinguished by detecting the pulse width or pulse waveform. Therefore, the measurement of particles in liquid is possible even though the liquid is chemically unstable and in which bubbles are easily generated. Further, control technique for particles in industrial chemical can be improved and the present invention can contribute to IC manufacture to be highly integrated.

DETAILED DESCRIPTION OF THE PREFERRED EMBODIMENTS

Figure 1:
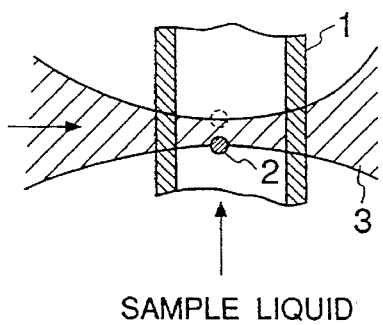
FIG. 1 is a sectional view showing the mechanism that a particle in sample liquid which passes through a flow cell passes through a laser beam irradiation region.
Figure 2:
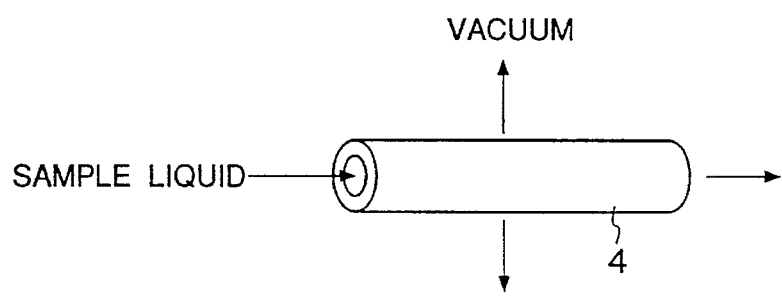
FIG. 2 is a view showing one example of conventional countermeasures to remove bubbles in sample liquid.
Figure 3:
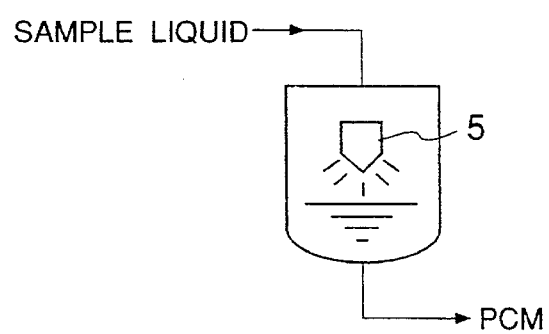
FIG. 3 is a view showing another example of conventional countermeasures to remove bubbles in sample liquid.
Figure 4:
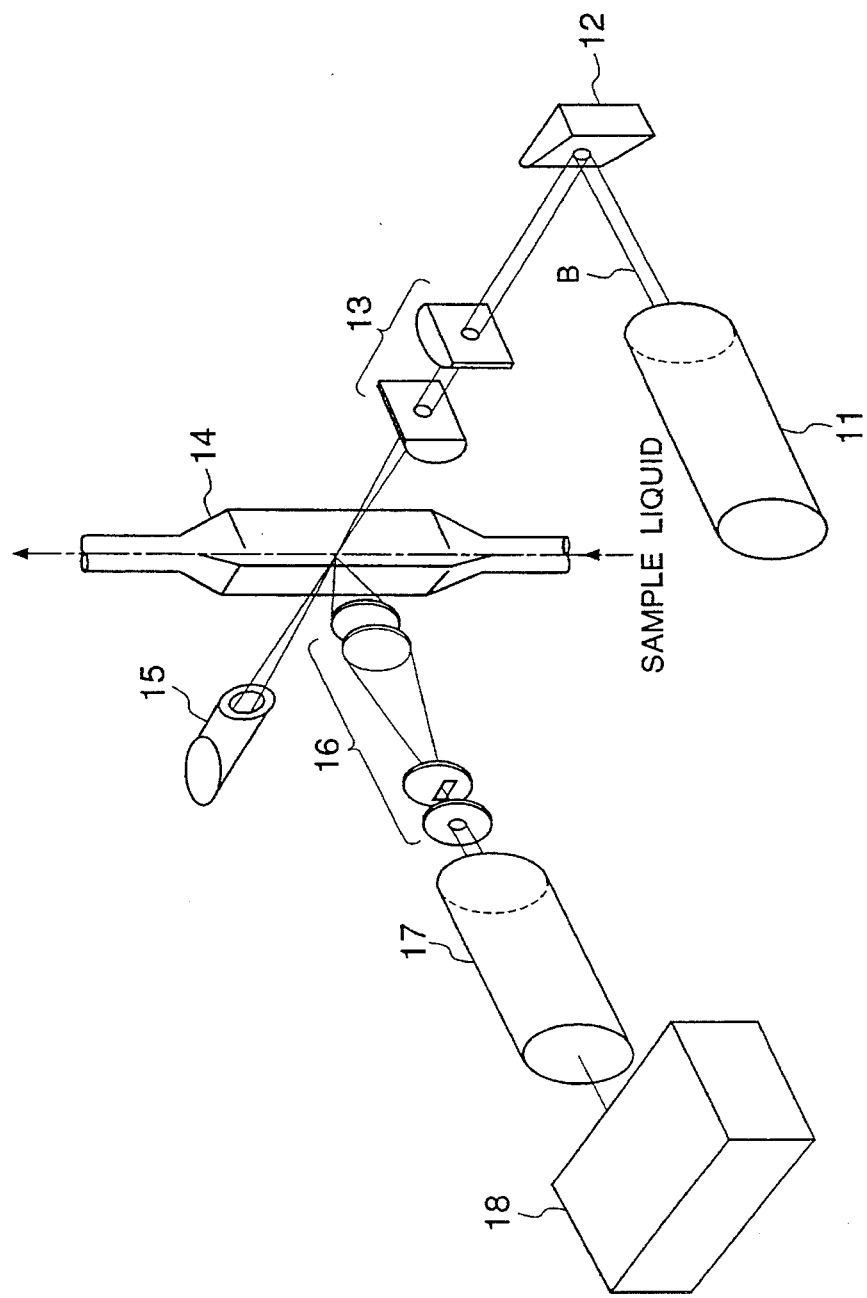
FIG. 4 is a perspective view showing a schematic configuration of a particle counting apparatus with use of a light scattering detecting method, which is used in each embodiment of the present invention.

FIG. 4 is a perspective view showing a particle counting apparatus to which a scattering light detecting method is used and which is used in each embodiment of the present invention, which will be described later.

Figures 5A, 5B, 5C:
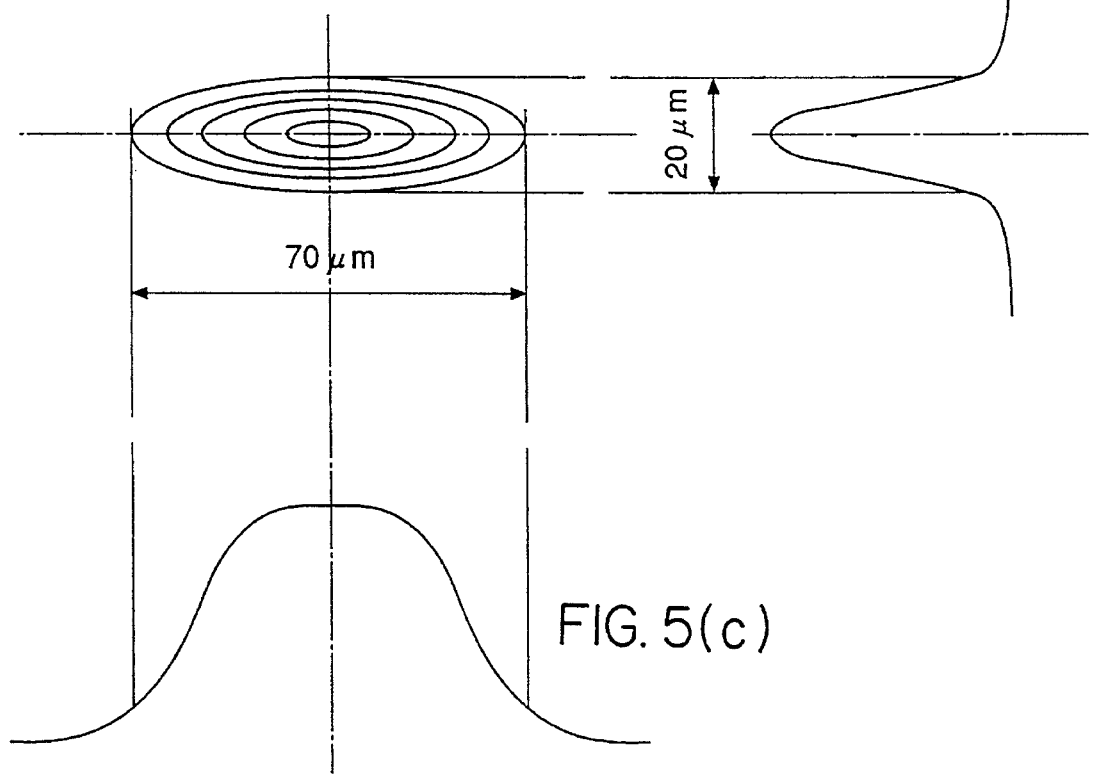
FIG. 5(a)–(c) are views showing a laser beam B irradiating from a laser source 11 in a particle counting apparatus shown in FIG. 4 to sample liquid in a flow cell 14.

A laser beam B is emitted from an He—Ne laser source 11, and its propagating direction is changed by an optical path changing mirror 12. The cross section of the laser beam B which is reflected by the mirror 12 is shaped into an ellipse by a shaping convergence lens 13. The laser beam B is shaped into a predetermined beam pattern, and then irradiates a to sample liquid which flows through a flow cell 14, and is converged on the sample liquid. The flow cell 14 is made of silica glass, sapphire, or others, and the sample liquid flows from the bottom to the top of the flow cell 14. The flow rate of the sample liquid is controlled at a fixed flow rate within a range of 10–200 cc/min. The laser beam B from the lens 13 is such that its energy intensity is the largest at a center of the flow cell 14 through which the sample liquid passes as shown in FIG. 5. Part (a) of FIG. 5 shows an elliptical cross section of the laser beam B, and part (b) of FIG. 5 shows a pattern of the beam intensity of the laser beam B in vertical direction, and part (c) of FIG. 5 shows a pattern of the beam intensity of the laser beam B in horizontal direction. As shown in FIG. 5, a length of the laser beam B in vertical direction corresponding to a flow direction of the sample liquid is 20 μm, and a length of the laser beam B in horizontal direction which is perpendicular to a flow direction of the sample liquid is 70 μm. The laser beam B thus converged into the sample liquid in the flow cell 14 is collected in a beam trap 15 and then disappears.

Figure 6:
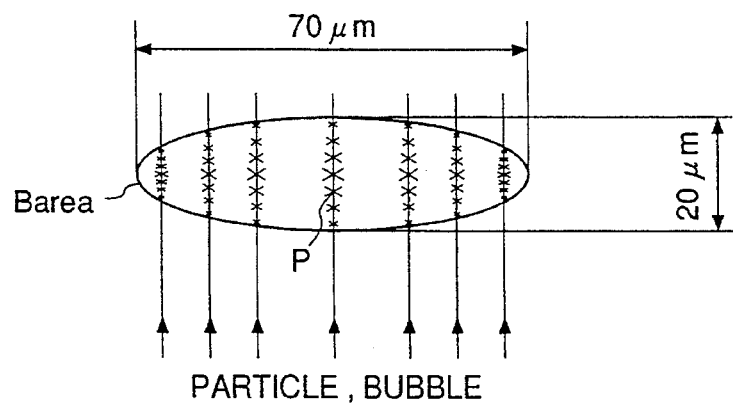
FIG. 6 is a view showing scattering light generation by particles or bubbles passing through a laser beam irradiation region $B_{area}$.

As shown in FIG. 6, when the particles and bubbles which are present in the sample liquid pass through a laser beam irradiation region $B_{area}$ in the flow cell 14, scattering light P, shown as X marks in FIG. 6, are generated. The light scattering P is generated with the intensities corresponding to a size of the particles in the liquid. The light scattering which is in the range required for the measurement is condensed by a light receiving optical system 16 provided in a direction perpendicular to an optical axis of the laser beam B. The condensed scattered light is led into a photoelectric convertor 17 which is constituted by a photomultiplier or others, and converted into electrical pulse signals. The pulse signals are entered to a signal processing apparatus 18, and distinguished into pulse signals corresponding to the particles in the sample liquid and pulse signals corresponding to the bubbles in the sample liquid, which will be described later.

The principle of the light scattering detecting method is expressed by a following equation. This principle is that as a diameter of a particle in liquid is about submicron, the light intensity $I_\theta$ of the scattering light P is proportional to the particle diameter D to the sixth power.

$$I_\theta = \{8\pi^4 \cdot I_0 \cdot D^6/(R^2 \cdot \lambda^4)\} \cdot |(n^2-1)/(n^2+2)|^2 \cdot (1+\cos^2\theta)$$

where $I_\theta$ is scattered light intensity, $I_0$ is laser beam B intensity, D is a diameter of a particle in liquid, R is a distance from a particle in liquid to an observation point, λ is a wavelength of a laser beam B, n is a ratio of a refractive index of a particle to a refractive index of liquid, and θ is a scattering angle measured from a propagating direction of a laser beam B (in this embodiment, θ is 90°).

Figure 7:
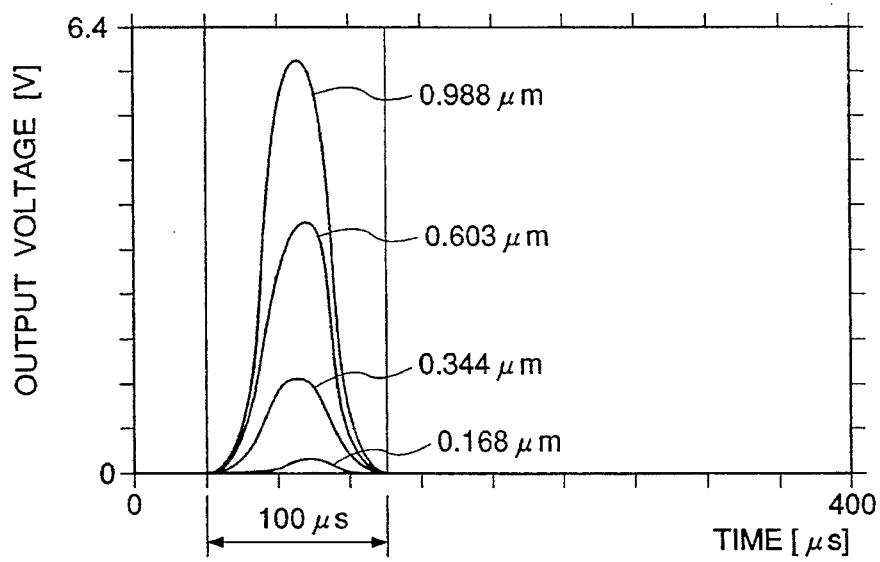
FIG. 7 is a graph showing a pulse signal obtained by photoelectrically converting light scattered by a particle in liquid.

The inventors observed a standard polystyrene-latex sphere which was mixed into super pure water as a particle by using this scattering light detecting method. That is, the inventors flowed this mixed liquid into the flow cell 14 as standard liquid at a fixed flow rate of 100 cc/minute. Then, they observed a time interval between the scattered light appearance generated by this standard sphere passing through the laser beam irradiation region $B_{area}$ and the scattered light disappearance with a synchroscope. FIG. 7 is a graph showing the results of the observation, and a horizontal line of the graph indicates a pulse width of a pulse signal obtained by the photoelectric convertor 17 in time [μS] and a vertical line thereof indicates a pulse signal height in an output voltage [V] of the photoelectric converter 17. Four kinds of the standard liquid were prepared with use of the standard sphere having four different of particle diameters 0.168 μm, 0.344 μm, 0.603 μm, and 0.988 μm. As a result of flowing each standard liquid into the flow cell 14, as shown in the graph, pulse signals having four kinds of the light scattering intensities corresponding to each particle diameter were obtained. As shown in the graph, a pulse width of the all pulse signals is within 100 μS, even though the particle diameter is different from each other. Note that one representative pulse signal corresponding to each particle diameter among the obtained pulse signals is shown. Further, waveform of each pulse signal waveform has one peak of the signal intensity in the fixed time interval.

Figure 8:
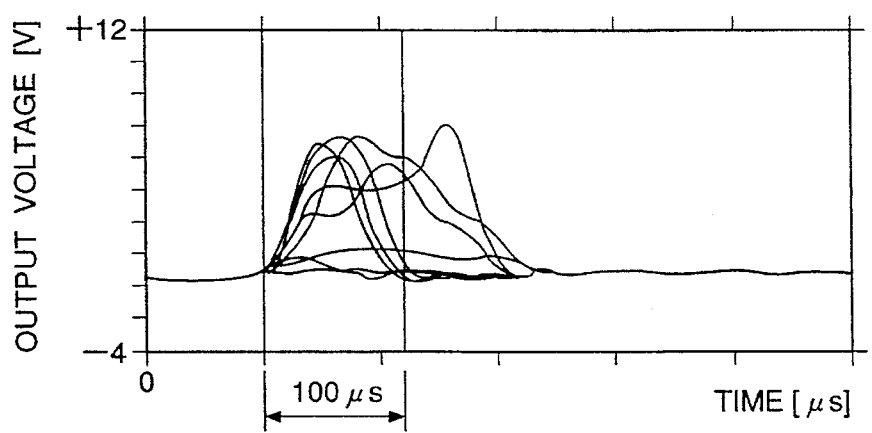
FIG. 8 is a graph showing a pulse signal obtained by photoelectrically converting light scattered by a bubble in liquid.

Next, purified air was dissolved in super pure water by a bubble generator which will be described later, and the sample liquid containing a certain amount of bubbles instead of the above-described standard sphere μS, flowed into the flow cell 14 under the same condition as the above-described condition. Then, pulse signals obtained by the photoelectric converter 17 corresponding to light scattered by the bubbles were observed by the synchroscope. FIG. 8 is a graph showing the results of this observation, and a horizontal line of the graph indicates a pulse width of a pulse signal obtained by the photoelectric generator 17 in time [μS], and a vertical line thereof indicates a pulse signal height in an output voltage [V] of the photoelectric converter 17. As shown in this graph, it can be understood that a pulse width of the pulse signals obtained corresponding to light scattered by the bubbles are out of the range of 100 μS, generally exceeding 100 μS, which is different from the pulse width of the pulse signals obtained corresponding to the particles. Further, it was found that the pulse signal waveform obtained corresponding to the bubbles was distorted, had no regularity, had a plurality of waves, which was different from the pulse signal waveform obtained corresponding to the particle.

Figure 9:
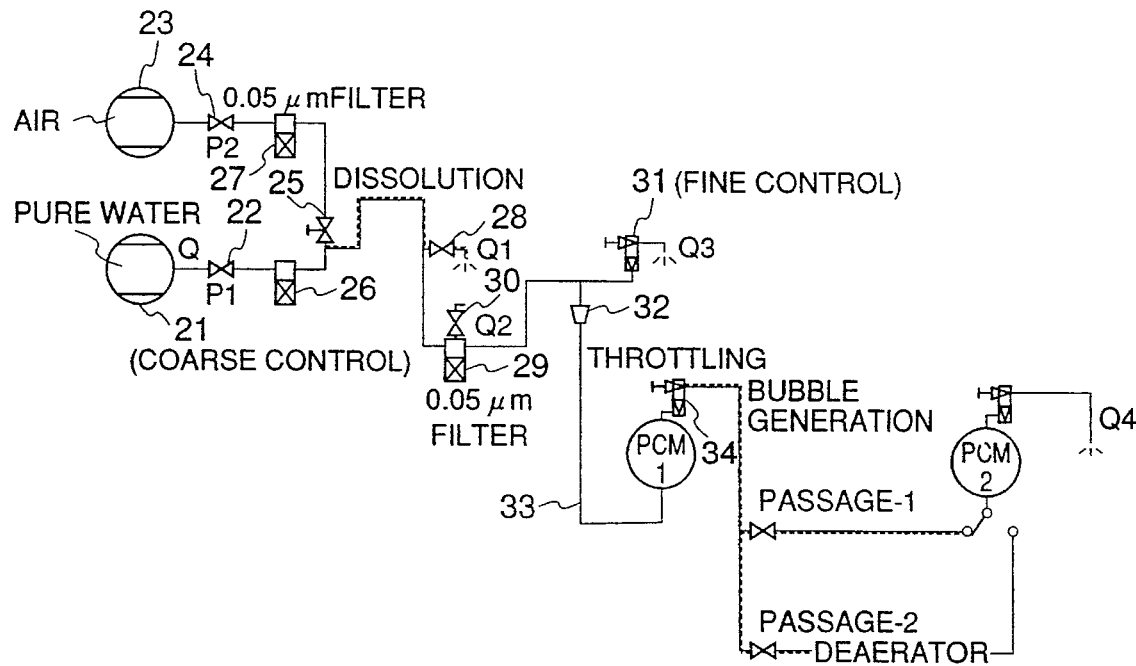
FIG. 9 is a schematic view showing a bubble generator.

Here, air dissolution in super pure water was performed by a bubble generator as shown in FIG. 9. That is, the super pure water of flow rate Q is provided to a fluororesin tube from a pure water supply apparatus 21. The super pure water in the tube is set to pressure P1 of 1.6 Kg/cm$^2$ by a pressure control valve 22. Further, air is provided to the similar tube from an air supply apparatus 23. The air in the tube is set to pressure P2 of 1.8 Kg/cm$^2$ by a pressure control valve 24 and then finely adjusted by a valve 25 for fine adjustment. The super pure water and air provided to each tube pass through filters 26 and 27, so that foreign substances which are larger than 0.05 μm are removed. The super pure water and air are mixed and then become the gas-liquid mixed condition. In FIG. 9, a part of the tube where a solid line and a dotted line are shown in parallel means the gas-liquid mixed line. The 20~30 cc/min (flow rate Q1) gas-liquid mixed material is led out from the air-liquid mixed line through a valve 28 to control the height of the super pure water surface in the tube. If the gas-liquid mixed material flows too much, the surface height sinks. Further, approximately 10 cc/min (flow rate Q2) gas is removed from a valve 30 which is provided at the top of a 0.05 μm filter 29. Further, approximately 100 cc/min (flow rate Q3) pure water is removed from a flow meter 31 with a flow rate adjustment apparatus, and air solubility in pure water is finely adjusted by adjusting a contact period of pure water and air. The pure water in which the certain amount of air is dissolved is led into a fluororesin tube 33 having a 6 mm outer diameter and a 4 mm inner diameter through a reducer 32, and the air solubility is measured by a particle counter PCM1. Further, the pure water pressure is reduced by a throttling bubble generator 34, so that bubbles are generated in pure water in the tube 33. The amount of air in pure water containing the bubbles is measured by a particle counter PCM2, and after the measurement, the 100 cc/min (flow rate Q4) sample liquid is obtained. Note that when the air solubility in pure water is measured by a particle counter PCM2 after the super pure water containing the bubbles is led to a deaerator, the air solubility is measured with the absence of bubbles. Then, the air solubility in super pure water can be detected in the both cases of the presence of bubbles and the absence of bubbles.

The total flow rate Q provided from the pure water supply 21 to the apparatus is a sum of the flow rates Q1~Q4, which is expressed by the following equation.

$Q=Q1+Q2+Q3+Q4$

Figure 10:
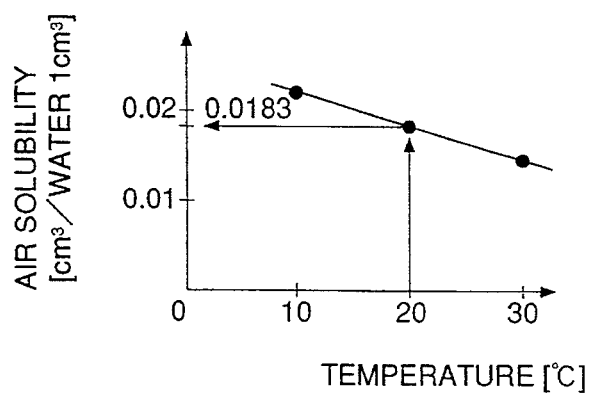
FIG. 10 is a graph showing air solubility in pure water.

FIG. 10 is a graph showing air solubility in super pure water under atmospheric pressure (1.01325×10$^5$ Pa). A horizontal line of the graph indicates temperature [°C.], and the vertical line indicates the air solubility per 1 cm$^3$ super pure water [cm$^3$/water 1 cm$^3$]. As shown in the graph, the air solubility under atmospheric pressure at 20° C. is 0.0183 cm$^3$ per 1 cm$^3$ water. Since the super pure water pressure is decreased to around the atmospheric pressure by the throttling bubble generator 34, the air which exceeds the air solubility among the air dissolved in the pure water under the pressure becomes bubbles mixed in the super pure water.

Figure 11:
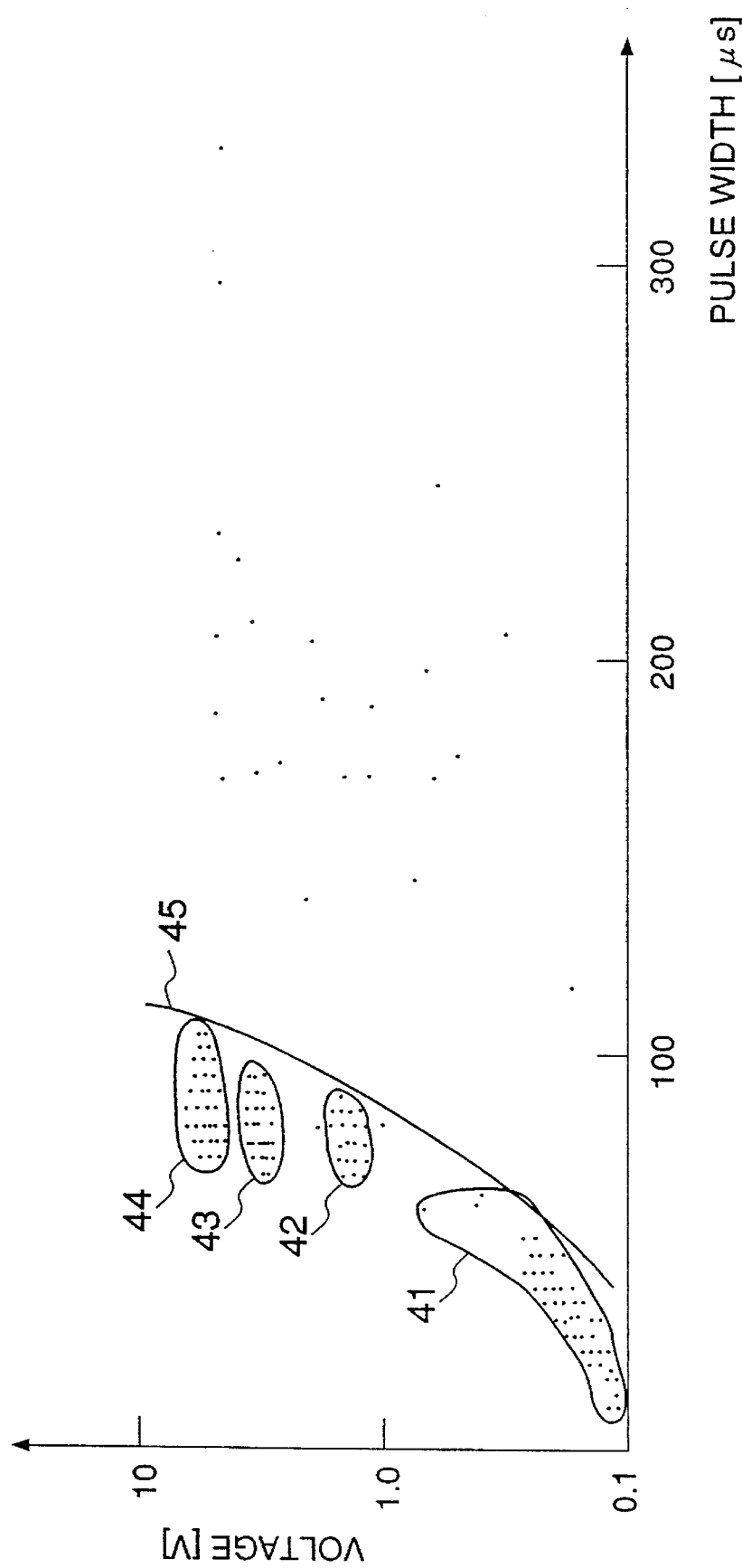
FIG. 11 is a graph showing a relation between a pulse height and a pulse width of a pulse signal obtained by converting light scattered by a particle and bubble in liquid.

Further, the inventors add a certain amount of the above-described standard polystyrene-latex sphere to thus generated sample liquid containing the bubbles, and flow the 100 cc/min bubble-particle mixed liquid into the flow cell 14, and irradiate a laser beam B to this mixed liquid. When the bubbles and particles pass through the laser beam irradiation region $B_{area}$, scattered light is generated, and this scattered light is are converted into pulse signals by the photoelectric converter 17. FIG. 11 is a graph showing the results of the pulse signal measurement. The horizontal line of the graph indicates a pulse width of a pulse signal [μS] and the vertical line indicates a pulse signal height in voltage [V]. A group of dots 41 shows pulse signals corresponding to light scattered by 0.168 μm diameter standard spheres. Groups of dots 42, 43, and 44 show pulse signals corresponding to 0.344 μm, 0.603 μm, and 0.988 μm diameter standard spheres, respectively. A group of dots to the right hand side of border line 45 in the graph shows pulse signals corresponding to light scattered by the bubbles. As shown in the graph, the pulse width of the all pulse signals corresponding to the standard spheres is within 100 μS except a part of the 0.988 μm standard spheres. Further, the pulse width of the all pulse signals corresponding to the bubbles exceeds 100 μS. Accordingly, for a submicron particle, as boundary is set on 100 μS, a pulse signal can be distinguished as to whether it corresponds to a particle or a bubble.

That is, a particle and a bubble can be distinguished by irradiating a laser beam B to liquid which flows at a fixed flow rate and contains particles and bubbles, converting the generated light scattering into pulse signals and detecting a pulse width of the pulse signals. Also, a particle and a bubble can be distinguished by the difference between the pulse signal waveform corresponding to a particle shown in FIG. 7, and the pulse signal waveform corresponding to a bubble shown in FIG. 8.

As is apparent from the above description, a pulse width of a pulse signal converted from light scattering is equivalent to the period of time of a particle or a bubble passing through the irradiation region.

A method of measuring particles and an apparatus for the same in accordance with the differentiating principle of the present invention will be explained in each embodiment. Liquid to be measured in the embodiments is, for example, water, sulfuric acid, nitric acid, phosphoric acid, and hydrofluoric acid or the like, in which air or nitrogen is contained as bubbles. The bubbles of nitrogen are used to maintain the pressure of each liquid, and are dissolved in each liquid. In addition, aqueous ammonia and ammonium fluoride, which contain air, nitrogen, or ammonium gas as bubbles are also the liquid to be measured. A saturating point of aqueous ammonia is 29 vol % (volume percentage) at 30° C., and without this condition, ammonium gas is generated. Further, hydrogen peroxide ($H_2O_2$) containing oxygen as bubbles is also the liquid to be measured. The bubble of oxygen is $O_2$, resulting from the decomposition of $H_2O_2$. In addition, resist solutions for semiconductor device manufacture, positive type developing solutions, and a low grade of alcohol that the number of carbons (C) is 1 to 4, in which nitrogen is contained as bubbles are also the liquid to be measured. The number of particles of submicron class in every liquid to be measured can be measured accurately in each embodiment of the present invention. Here, the flow rate of the liquid to be measured in the flow cell 14 is 100 cc/min in common in every embodiment.

Figure 12:
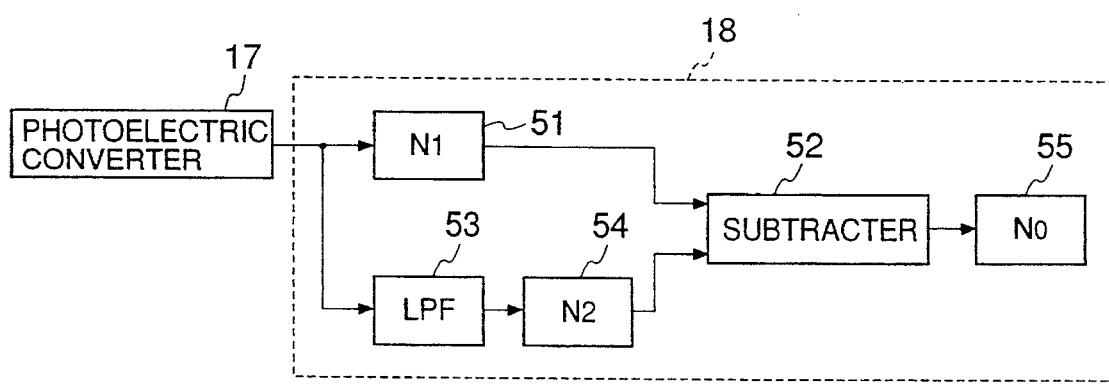
FIG. 12 is a block diagram showing one example of an internal configuration of a signal processing apparatus 18 which is used in the first embodiment of the present invention.
Figure 13:
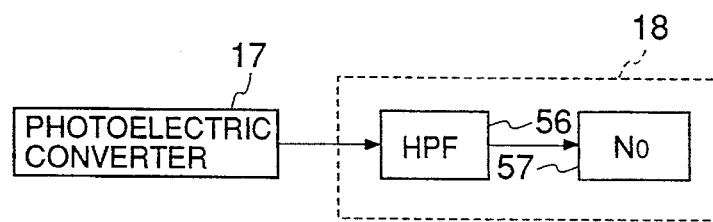
FIG. 13 is a block diagram showing another example of an internal configuration of a signal processing apparatus 18 which is used in the first embodiment of the present invention.

FIG. 12 and FIG. 13 are block diagrams, each showing an internal configuration of a signal processing apparatus 18 which is used in the first embodiment of the present invention, and the total configuration of the particle measuring apparatus is shown in FIG. 4.

One of the above-described liquid to be measured flows into the flow cell 14 at the above-described fixed flow rate, and a laser beam B irradiates liquid. The particles and bubbles pass through the laser beam irradiation region $B_{area}$ in the flow cell 14, whereby the light scattering is generated, and the light scattering is converted into pulse signals by a photoelectric converter 17. The pulse signal is provided to a total counter (N1) 51 shown in FIG. 12 in the signal processing apparatus 18, and the number of the all pulse signals photoelectrically converted by the photoelectric converter 17 is counted. The result of the counting shows the sum of the number of particles and the number of bubbles, and is output to a subtracter 52. Further, the pulse signal output from the photoelectric converter 17 is also applied to a low-pass filter circuit (LPF) 53, and only the pulse signals having a pulse width which is larger than 100 μS are selected and outputted to a bubble counter (N2) 54. The bubble counter 54 counts the pulse signal applied thereto. The result of the counting is equivalent to the number of bubbles in the liquid to be measured and outputted to the subtracter 52. The subtracter 52 subtracts the counted number which is outputted from the bubble counter 54 from the counted number which is output from the total counter 51, and outputs this result of the subtraction to a particle counter 55. The particle counter 55 outputs this result of the counting to the outside of the apparatus as the number of particles in liquid.

In the first embodiment, the number of particles is measured by detecting pulse signals having a pulse width which is larger than 100 μS among the total number of pulse signals which are output from the photoelectric converter 17, but it is possible to measure the number of particle in the following way. That is, as shown in FIG. 13, a pulse signal output of the photoelectric converter 17 is applied to a high-pass filter circuit (HPF) 56, and the pulse signals having a pulse width which is less than 100 μS are selected and applied to a particle counter 57. The particle counter 57 counts the number of pulse signals applied thereto, and outputs this result of the counting to the outside of the apparatus as the number of the particles in liquid.

In this embodiment, the pulse signals corresponding to the bubbles in liquid are selected in the low-pass filter circuit 53, and the pulse signals corresponding to the particles in liquid are selected in the high-pass filter circuit 56, so that the particles in the liquid can be distinguished from the bubbles in the liquid, and the number of particles in the liquid can be measured accurately.

Figure 14:
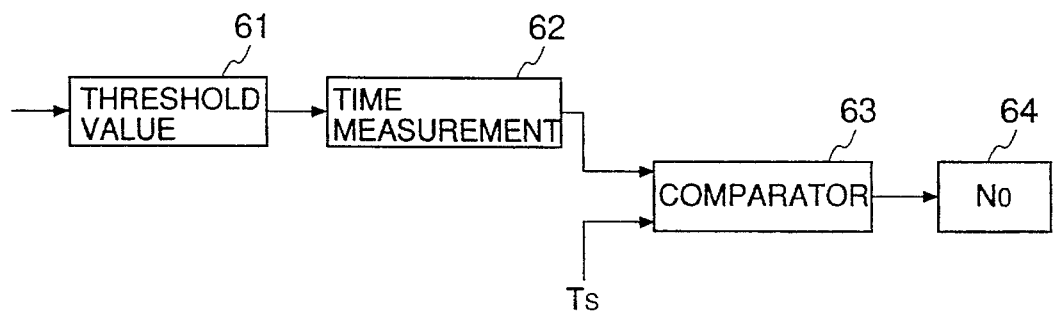
FIG. 14 is a block diagram showing an internal configuration of a signal processing apparatus 18 which is used in the second embodiment of the present invention.

Next, FIG. 14 is a block diagram showing an internal configuration of a signal processing apparatus 18 which is used in the second embodiment of the present invention. Similar to the first embodiment, the total configuration of the particle measuring apparatus is shown in FIG. 4.

In the second embodiment, pulse signals outputted from a photoelectric converter 17 are applied to a threshold circuit 61 in a signal processsing circuit 18. The threshold circuit 61 outputs a rectangular pulse signal having a predetermined pulse width to a time measurement circuit 62. The predetermined pulse width corresponds to a period from the input pulse signal intensity exceeding a predetermined threshold value to going back below the same threshold value. The time measurement circuit 62 measures the pulse width of the rectangular pulse signal, and the result of the measurement is outputted to a comparator 63. A standard time $T_s$ which is determined in accordance with the flow rate of the liquid to be measured flowing in the flow cell 14 is applied to the comparator 63. That is, in a case that the liquid to be measured flows at the specified flow rate, a duration of a particle in liquid passing through a laser beam irradiation region $B_{area}$ is a known value, and this value is applied to the comparator 63 as the standard time $T_s$. In the present embodiment, since the flow rate of the particles in the liquid which flows in the flow cell 14 is 100 cc/min as described above, the standard time $T_s$ in which the particles in the liquid pass through the laser beam irradiation region is 100 μS. The comparator 63 compares the result of the measurement of the applied pulse width applied from the time measurement circuit 62 with the standard time $T_s$ and outputs only the pulse signals having a pulse width which is less than the standard time $T_s$ to a particle counter (No) 64. The particle counter 64 counts the number of pulse signals which are less than the standard time $T_s$, and outputs the result of the counting as the number of particles in liquid.

Figure 15:
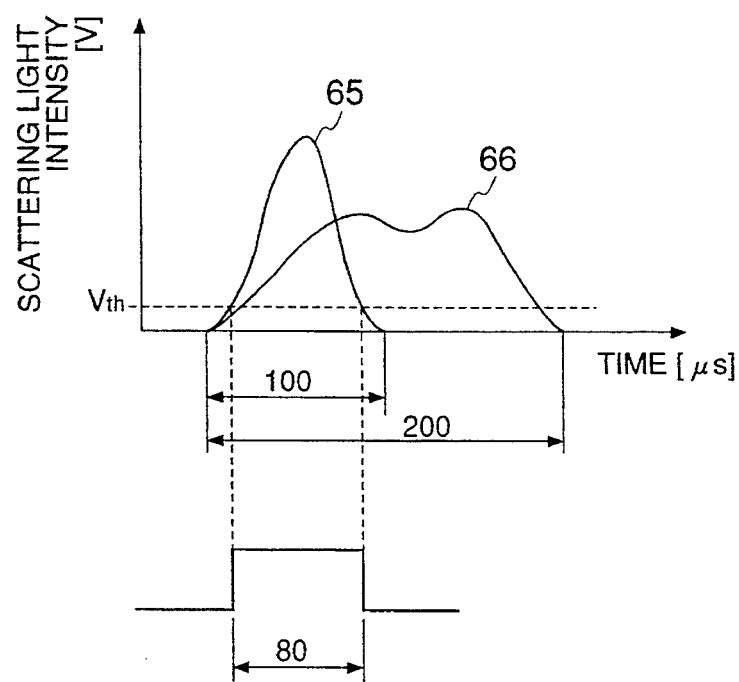
FIG. 15 is a graph showing a pulse signal which is entered to a signal processing apparatus 18 which is used in the second embodiment of the present invention.

For example, in a case that a pulse signal shown in a graph of FIG. 15 is applied to a threshold circuit 61 from the photoelectric converter 17, the particle measurement is performed in the following way. Note that the horizontal line of the graph is time [μS], and that the vertical line thereof is a pulse voltage height [V] corresponding to the light scattering intensity. First, a case that a pulse signal 65 corresponding to a particle in liquid having a signal time of 100 μS from rising to falling, is applied will be explained. In this case, the threshold circuit 61 generates a rectangular pulse signal having a predetermined pulse width shown in FIG. 15. The predetermined pulse width corresponds to a period from the pulse height exceeding the threshold value $V_{th}$ to going back below the threshold value $V_{th}$, and is 80 μS. Note that the threshold value $V_{th}$ is suitably adjusted to a proper value. The 80 μS pulse width of the rectangular pulse signal is measured by the time measurement circuit 62, and is outputted to the comparator 63. The comparator 63 compares the 80 μS pulse width and the 100 μS standard time $T_s$. In this case, since the pulse width is shorter, the comparator 63 outputs the input pulse signal to the particle counter 64. The particle counter 64 regards the input pulse signal as corresponding to the particle in the liquid, and then increments the counted value.

Further, a case that a pulse signal 66 corresponding to a bubble in liquid, of which signal time from rising to falling is 200 μS is applied will be explained. In this case, the threshold circuit 61, as well as above mentioned case, generates a rectangular pulse signal having a predetermined pulse width. The predetermined pulse width corresponds to a period while the pulse height exceeding the threshold value $V_{th}$. The pulse width of the rectangular pulse signal is measured by the time measurement circuit 62, and is compared with the standard time $T_s$ by the comparator 63. In this case, since the pulse width is longer, the comparator 63 does not output the input pulse signal to the particle counter 64. Accordingly, the counted value in the particle counter 64 is not changed.

In the second embodiment, the pulse width of the input pulse signal is compared with the known standard time which is determined in accordance with the flow rate of the liquid to be measured, so that the particle and bubble can be distinguished.

Figure 16:
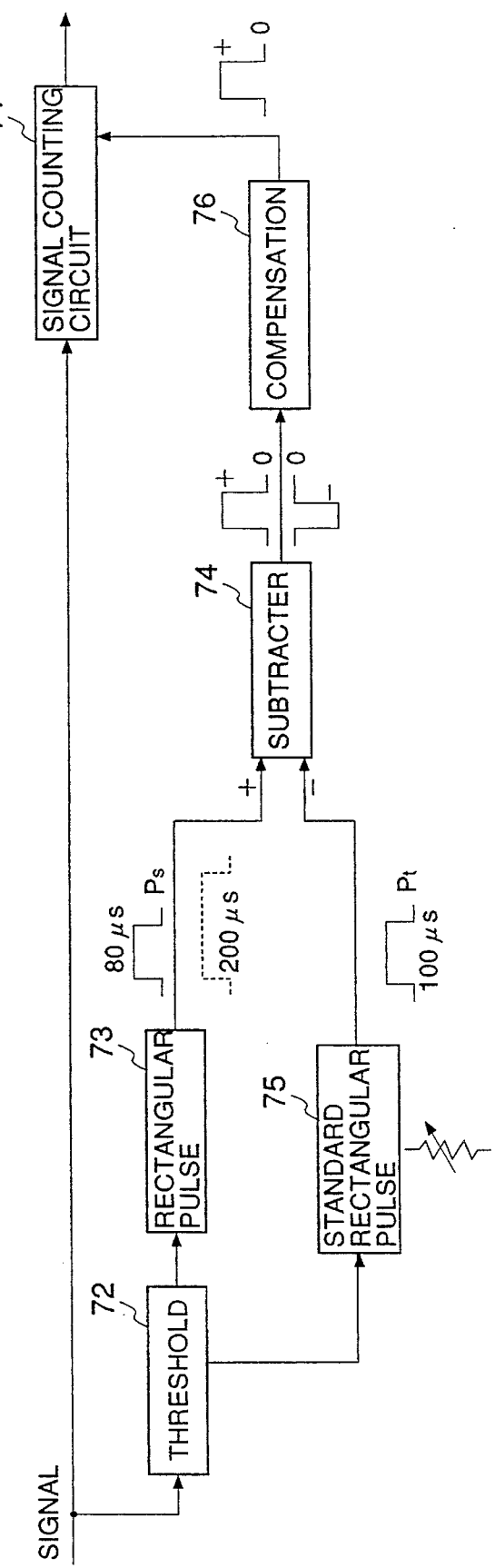
FIG. 16 is a block diagram showing an internal configuration of a signal processing apparatus 18 which is used in the third embodiment of the present invention.

Next, FIG. 16 is a block diagram showing an internal configuration of a signal processing apparatus 18 which is used in the third embodiment of the present invention.

Similar to the first embodiment, the total configuration of the particle measurement apparatus is shown in FIG. 4.

In the third embodiment, a pulse signal outputted from a photoelectric converter 17 is applied to a signal counting circuit 71 in the signal processing circuit 18, and the number of the all pulse signals corresponding to particles and bubbles photoelectrically converted by the photoelectric converter 17 is counted. The pulse signal output from the photoelectric converter 17 is also applied to a threshold circuit 72. The threshold circuit 72 detects the time at which an input pulse signal height exceeds a predetermined threshold value $V_{th}$ and the time at which the input pulse signal height goes back to the threshold value $V_{th}$. A rectangular pulse generation circuit 73 inputs these timing signals, generates a rectangular pulse signal $P_s$ having a predetermined pulse width which corresponds to a period while the input pulse signal exceeding the threshold value $V_{th}$, and outputs this rectangular pulse signal $P_s$ to a subtracter 74. Further, a standard rectangular pulse signal generation circuit 75 inputs the timing signal at which the pulse signal height exceeds the threshold value $V_{th}$ from the threshold circuit 72, and this timing signal triggers the standard rectangular pulse signal $P_t$ generation having the specified time width. The specified time width can be set arbitrarily, and the generated standard rectangular pulse signal $P_t$ is outputted to the subtracter 74. The subtracter 74 subtracts the standard rectangular pulse signal $P_t$ which is outputted from the standard rectangular pulse signal generation circuit 75 from the rectangular pulse signal $P_s$ which is outputted from the rectangular pulse signal generation circuit 73. The result of the subtraction is applied to a compensating circuit 76, and the compensating circuit 76 detects the polarity of the pulse signal resulting from the subtraction.

When the polarity of the pulse signal resulting from the subtraction is positive, since the pulse width of the input pulse signal is longer than the specified time, the input pulse signal corresponds to the light scattered by the bubble in the liquid, and then a compensating signal is outputted to a signal counting circuit 71. When the signal counting circuit 71 received the compensating signal, the signal counting circuit 71 subtracts one from the counted value, and compensates the counted value by removing the number of bubbles from the counted value of the signal counting circuit 71. The pulse width of the compensating signal which is outputted from the compensating circuit 76 to the signal counting circuit 71 is equivalent to a period for which the pulse width of the rectangular pulse signal $P_s$ exceeds the pulse width of the standard rectangular pulse signal $P_t$, and a counting function of the signal counting circuit 71 is stopped contemporarily during the compensating signal is applied. Due to the stop of the counting function, error in measurement caused by the pulse signal input corresponding to the continuous large bubbles is prevented. When the polarity of the pulse signal resulting from the subtraction is negative, the pulse width of the input pulse signal is shorter than the specified time. Therefore, the compensating circuit 76 decides that the input pulse signal corresponds to the light scattered by the particles in the liquid and does nothing thereto.

For example, in a case that a pulse signal which has a signal time of 100 μS from rising of the signal to falling of the signal, and which corresponds a particle in the liquid is applied to the signal processing circuit 18, the rectangular pulse signal generation circuit 73 generates a rectangular pulse signal $P_s$ having a 80 μS pulse width. The standard rectangular pulse signal generation circuit 75 generates a standard rectangular pulse signal $P_t$ having a 100 μS pulse width. The 100 μS pulse width is a specified width corresponding to a 100 cc/min fixed flow rate of the liquid to be measured in the flow cell 14. The subtracter 74 subtracts the standard rectangular pulse signal $P_t$ from the rectangular pulse signal $P_s$, and outputs the pulse signal of the negative polarity having a 20 μS pulse width. Since the polarity of the input pulse signal is negative, the compensating circuit 76 does nothing thereto. Therefore, the value counted in the signal counting circuit 71 is output as the number of the particles in the liquid without any changes.

On the other hand, in a case that a pulse signal corresponding to a bubble in the liquid is applied to the signal processing circuit 18, it is assumed that the rectangular pulse signal generation circuit 73 generates a rectangular pulse signal $P_s$, e.g., having a 200 μS pulse width. In this case, the standard rectangular pulse signal generation circuit 75 also generates a standard rectangular pulse signal $P_t$ having a 100 μS pulse width. The subtracter 74 subtracts the standard rectangular pulse signal $P_t$ from the rectangular pulse signal $P_s$, and outputs a pulse signal of the positive polarity having a 100 μS pulse width. Since the polarity of the input pulse signal is positive, the compensating circuit 76 outputs a compensating signal of the positive polarity having a 100 μS pulse width to the signal counting circuit 71. The signal counting circuit 71 inputs the compensating Signal and then outputs a counted value, in which one is subtracted from the counted value, as the number of particles in the liquid. Further, simultaneously, while the 100 μS compensating signal is applied, the signal counting circuit 71 stops counting the input pulse signal from the photoelectric converter 17 temporarily.

According to the third embodiment, a standard rectangular pulse signal $P_t$ having a specified time width is subtracted from a rectangular pulse signal $P_s$ having a pulse width corresponding to an input pulse signal, and based on the polarity of the pulse signal resulting from the subtraction, the particles and the bubbles are distinguished. In addition, when there is the input corresponding to the bubble, while the signal is outputting from the compensating circuit 76, the counting function of the signal counting circuit 71 is stopped temporarily, so that error in measurement caused by continuous large bubble inputs is prevented.

Figure 17:
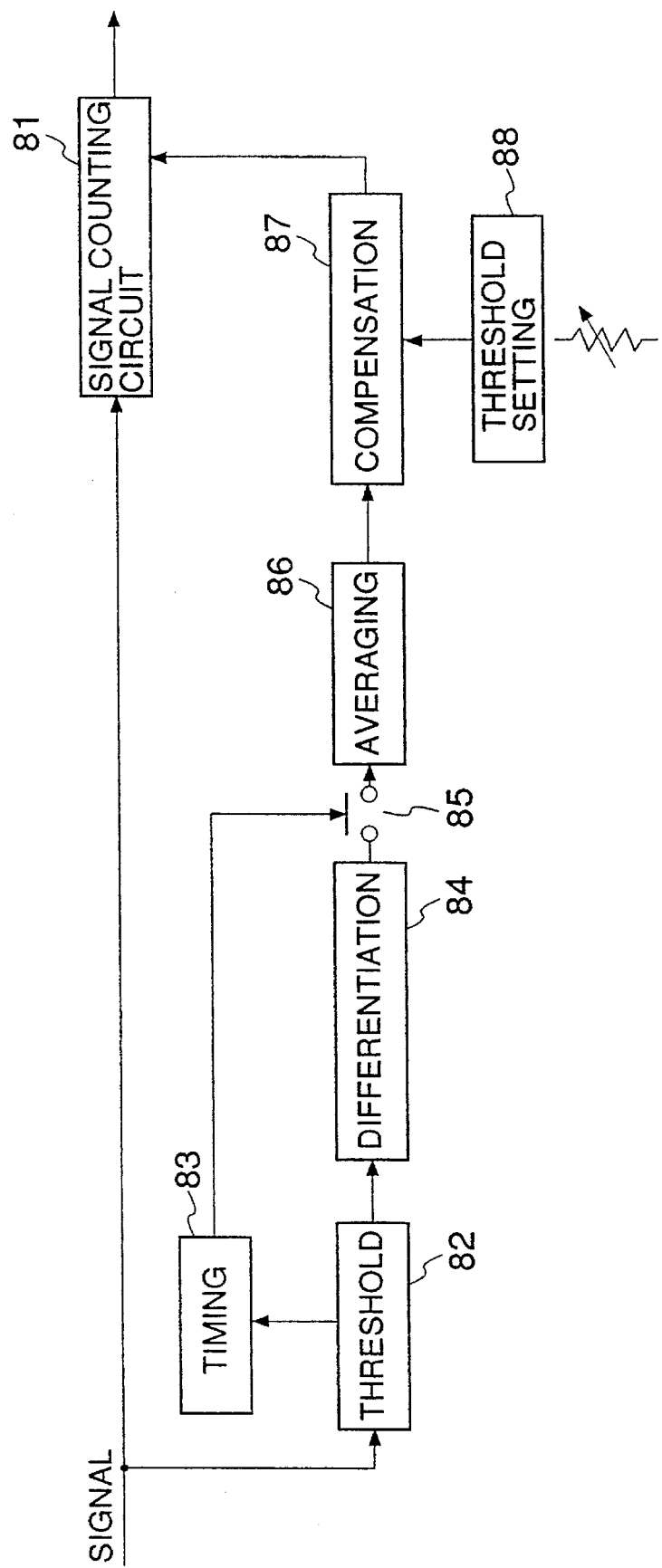
FIG. 17 is a block diagram showing an internal configuration of a signal processing apparatus 18 which is used in the fourth embodiment of the present invention.

Next, FIG. 17 shows a block diagram of an internal configuration of a signal processing apparatus 18 which is used in the fourth embodiment of the present invention. Similar to the first embodiment, the total configuration of the particle measuring apparatus is shown in FIG. 4.

A pulse signal output from a photoelectric converter 17 is applied to a signal counting circuit 81, and the number of all pulse signals corresponding to light scattered by particles and bubbles is counted. The pulse signal output from the photoelectric converter 17 is also applied to a threshold circuit 82. The threshold circuit 82 outputs a trigger signal to a timing circuit 83 when the input pulse signal exceeds the threshold value $V_{th}$ which is set in advance. The timing circuit 83 is activated by this trigger signal input, and a switch 85 is turned on for a fixed period starting from the trigger signal being applied, e.g., in this embodiment, 100 μS. The pulse signal passing through the threshold circuit 82 from the photoelectric converter 17 is differentiated in a differentiating circuit 84, and is loaded into an averaging circuit 86 through the switch 85. The differentiated signal in a period of 100 μS starting from the input pulse signal exceeding the threshold value $V_{th}$ are loaded into the averaging circuit 86 within the differentiated signal which are output from the differentiating circuit 84 by controlling an on/off of the switching circuit 85. The averaging circuit 86 averages the input differentiated signals, and outputs the result of the averaging to a compensating circuit 87. A fixed threshold value from a threshold setting circuit 88 is outputted to the compensating circuit 87. The threshold value is suitably set to a proper value. The compensating circuit 87 compares the input averaged value with the threshold value applied from the threshold setting circuit 88, and if the averaged value exceeds the threshold value, the compensating circuit 87 outputs a pulse signal Sx to the signal counting circuit 81. When the pulse signal Sx is applied, the signal counting circuit 81 determines that the input pulse signal from the photoelectric converter 17 corresponds to light scattered by a bubble in the liquid, and subtracts one from the counted value. Then, the signal counting circuit 81 outputs the result of the subtraction, which corresponds to the number of particles in the liquid.

Figure 18A:
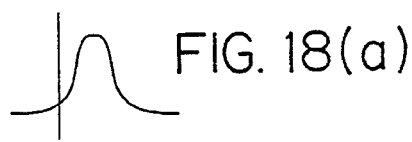
FIG. 18(a) and (b) are views showing a pulse signal which is entered to a signal processing apparatus 18 which is used in the fourth embodiment of the present invention.
Figure 18B:
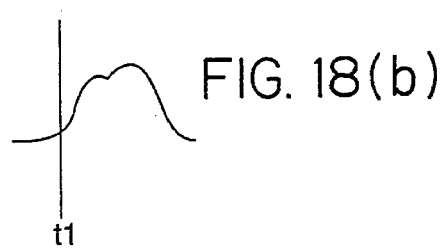

For example, it is assumed that a pulse signal comprises a single which wave shown in part (a) of FIG. 18 is obtained by the photoelectric converter 17 corresponding to a particle in the liquid. When the pulse signal is applied to the threshold circuit 82, a trigger signal is outputted to a timing circuit 83 at the timing of t1. When the input pulse signal shown in part (a) of FIG. 18 is differentiated by the differentiating circuit 84, the input pulse signal is converted into a differentiated signal having waveform shown in part (a) of FIG. 19. The signal component of the differentiated signal within 100 μS between the timing t1 and the timing t2 is outputted to the averaging circuit 86, with the timing circuit 83 controlling the switch 85. There is no signal component present within a period between the timing t2 and t3. The differentiated signal component between the timing t1 and t2 is averaged by the averaging circuit 86. Since the differentiated signal therebetween includes the equal positive and negative signal components, the result of the averaging by the averaging circuit 86 is zero output between t1 and t2 as shown in part (a) of FIG. 20. Accordingly, as a result of the comparison in the compensating circuit 87 between the averaged value and the threshold value, the threshold value is larger, and the compensating circuit 87 does not generate a pulse signal Sx. Therefore, the signal counting circuit 81 outputs the counted value as the number of particles in the liquid without any changes.

Figure 19A:
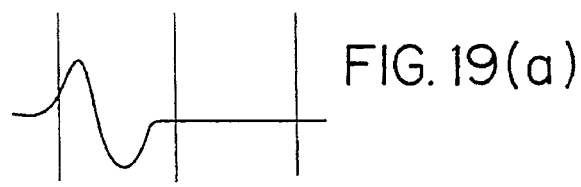
FIG. 19(a) and (b) are views showing a signal output from a differentiating circuit 84 in a signal processing apparatus 18 which is used in the fourth embodiment of the present invention.
Figure 19B:
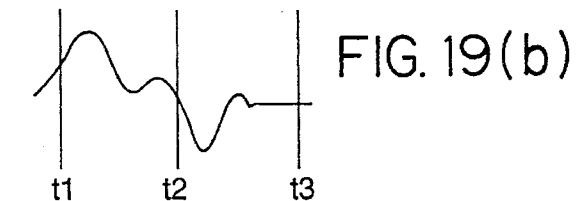
Figure 20A:
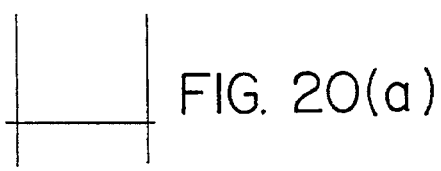
FIG. 20(a) and (b) are views showing a signal output from an averaging circuit 86 in a signal processing apparatus 18 which is used in the fourth embodiment of the present invention.
Figure 20B:
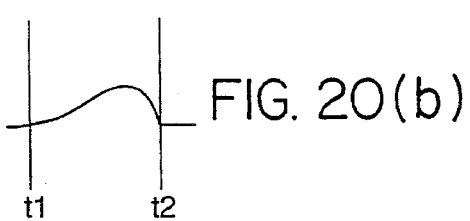
Figure 21:
FIG. 21 is a view showing a signal output from a compensating circuit 87 in a signal processing apparatus 18 which is used in the fourth embodiment of the present invention.

On the other hand, a pulse signal which comprises a plurality of waves shown in part (b) of FIG. 18 is obtained in the photoelectric converter 17, the threshold circuit 82 outputs a trigger signal to the timing circuit 83 when the input pulse signal exceeds the fixed threshold value $V_{th}$ as well as above mentioned case. When the input pulse signal is differentiated by the differentiating circuit 84, the differentiated signal the waveform of which is shown in part (b) of FIG. 19 is obtained. The signal components within 100 μS between the timing t1 and t2 in the differentiated signal are applied to the averaging circuit 86, and then the averaged value shown in part (b) of FIG. 20 is obtained. The input pulse signal corresponding to a bubble has many inflection points, and since the positive and negative components of the differentiated signal are not equal within 100 μS which is set by the timing circuit 83, as a result of the averaging, a positive output is obtained. This averaged value is compared with the threshold value by the compensating circuit 87. In this case, since the result of the averaging is larger than the threshold value, the compensating circuit 87 generates a pulse signal Sx shown in FIG. 21, and outputs the pulse signal Sx to the signal counting circuit 81. The signal counting circuit 81 subtracts one from the counted value in accordance with the pulse signal Sx inputting to compensate the counted value and then outputs the counted value.

The input pulse signal to be photoelectrically converted corresponding to a particle has waveform shown in FIG. 7, and since its inflection point is one, positive and negative components of a differentiated signal within 100 μS which is obtained by differentiating the input pulse signal, are substantially equal. Accordingly, when the differentiated signal is averaged, the averaged value is substantially zero. On the other hand, the input pulse signal to be photoelectrically converted corresponding to a bubble has waveform shown in FIG. 8, and since its inflection point is plural, positive and negative components of the differentiated signal within 100 μS which is obtained by differentiating the input pulse signal, are different from each other. Accordingly, when the differentiated signal is averaged, the averaged value is a certain value. Therefore, as in this embodiment, the averaged value of the differentiated signal is compared with the fixed threshold value, so that it can be distinguished that whether the input pulse signal corresponds to a particle or a bubble in liquid. As a result, the counted value corresponding to bubbles can be omitted from the counted value of the signal counting circuit 81, and only the number of particles in liquid can be measured.

What is claimed is:

1. An apparatus for measuring the number of particles in liquid, comprising:

a passage for liquid containing particles flowing at a fixed flow rate;

light source for irradiating a region of said liquid flowing through said passage;

light detecting means for converting scattered light from said irradiated liquid into pulse signals;

pulse width detecting means for detecting a pulse width of a pulse signal output from said light detecting means;

selecting means for selecting a pulse signal having a pulse width larger than a predetermined value from said pulse signals detected by said light detecting means;

a total counter for counting the total number of pulse signals output from said light detecting means;

a bubble counter for counting the selected pulse signals; and arithmetic means for subtracing a result of the counting of said bubble counter from a result of the counting of said total counter to calculate the number of particles in said liquid.

2. An apparatus according to claim 1, wherein said selecting means comprises a filter for selecting a pulse signal having a pulse width larger than a predetermined value.

3. An apparatus according to claim 1, wherein said selecting means comprises:

rectangular pulse generating means for generating a rectangular pulse signal having a pulse width of a value for which the pulse signal height exceeds a predetermined threshold value;

standard rectangular pulse generating means for generating a standard rectangular pulse signal having a pulse width of a value for which a standard particle passes through said irradiation region when the pulse signal height exceeds said predetermined threshold value;

comparing means for comparing the pulse width of said rectangular pulse signal with the pulse width of said standard rectangular pulse signal; and compensating means for subtracting one count from the counted value of said total counter to calculate the number of particles in said liquid for each rectangular pulse signal having a pulse width which exceeds the pulse width of said standard rectangular pulse signal.

4. An apparatus according to claim 3, wherein said compensating means stops said total counter counting temporarily when the pulse width of the rectangular pulse signal exceeds the pulse width of said standard rectangular pulse signal.

5. A method of measuring the number of particles in a liquid comprising steps of:

flowing a liquid containing particles and bubbles at a fixed rate:

irradiating a region of the liquid with a laser beam;

converting scattered light from the irradiated liquid, generated by the irradiating beam, into pulse signals;

counting the number of said pulse signals;

selecting pulse signals having pulse widths larger than a predetermined value, corresponding to light scattered by said bubbles in the liquid; and subtracting the number of the pulse signals selected in said selecting step from the number obtained in said counting step, whereby a result of the subtraction is the number of particles in said liquid.

6. A method of measuring the number of particles according to claim 5, wherein the step of selecting the pulse signal comprises steps of:

generating a rectangular pulse signal having a pulse width of a value for which a height of said pulse signal exceeds a predetermined threshold value;

generating a standard rectangular pulse signal when the pulse signal height exceeds said predetermined threshold value having a pulse width of a value for standard particles passing through said laser beam irradiation region; and comparing the pulse width of said rectangular pulse signal with the pulse width of said standard rectangular pulse signal.

7. The method according to claim 6, wherein the step of subtracting from the pulse signal comprises a step of:

subtracting from the number of said pulse signals counted in said counting step the number of rectangular pulse signals having pulse widths which exceed the pulse width of said standard rectangular pulse signal, whereby a result of the subtraction is the number of particles in said liquid.

8. A method of measuring the number of particles according to claim 6, wherein counting is stopped whenever the pulse width of the rectangular pulse signal exceeds the pulse width of said standard rectangular pulse signal.

9. A method of measuring a number of particles in a liquid, comprising:

flowing a liquid containing particles at a fixed flow-rate;

irradiating a portion of said liquid with a laser beam;

converting light scattered from the irradiated portion of said liquid into electrical pulse signals;

counting a number of particles in said liquid by counting said electrical pulse signals and excluding any pulse signals representing bubbles in said liquid.

10. The method according to claim 9, wherein the bubbles are identified as pulse signals having pulse widths larger than a predetermined value.

11. The method according to claim 10, wherein said bubbles are identified as rectangular pulse signals having pulse widths of a value for which a height of said pulse signal exceeds a predetermined threshold value, as compared to a standard rectangular pulse width signal generated when the pulse signal of a standard size particle, passing through said laser beam, exceeds said predetermined threshold value.

12. The method according to claim 11, wherein pulse signals with pulse widths larger than the standard rectangular pulse width are not counted.

13. The method according to claim 9, wherein said number of particles is counted by counting a total number of pulse signals and subtracting the number of pulse signals representing bubbles.

* * * * *